United States Patent [19]

Gleeson

[11] Patent Number: 5,271,013
[45] Date of Patent: Dec. 14, 1993

[54] FAULT TOLERANT COMPUTER SYSTEM

[75] Inventor: Barry J. Gleeson, Palo Alto, Calif.

[73] Assignee: Unisys Corporation, Blue Bell, Pa.

[21] Appl. No.: 521,283

[22] Filed: May 9, 1990

[51] Int. Cl.$^5$ .............................................. G06F 11/00
[52] U.S. Cl. ...................................... 371/9.1; 371/8.1;
371/12; 395/575
[58] Field of Search .................... 371/9.1, 8.1, 7, 12;
364/268.2; 395/575

[56] References Cited

U.S. PATENT DOCUMENTS

| | | | |
|---|---|---|---|
| 4,503,535 | 3/1985 | Budde et al. | 371/11 |
| 4,590,554 | 5/1986 | Glazer et al. | 364/200 |
| 4,775,976 | 10/1988 | Yokoyama | 371/9 |
| 4,819,154 | 4/1989 | Stiffler et al. | 371/7 |
| 4,819,159 | 4/1989 | Shipley et al. | 364/200 |
| 4,823,256 | 4/1989 | Bishop et al. | 364/200 |
| 4,958,273 | 9/1990 | Anderson et al. | 364/200 |

FOREIGN PATENT DOCUMENTS

| | | | |
|---|---|---|---|
| 55-80170 | 6/1980 | Japan | 371/9.1 |
| 57-5162 | 1/1982 | Japan | 371/9.1 |

OTHER PUBLICATIONS

FTCS 18, Digest of Papers, Jun. 27-30, 1988, Tokyo, Japan, pp. 44-49, R. E. Strom, et al., "Volatile Logging in N-Fault-Tolerant Distributed Systems".
FTCS 17, Digest of Papers, Jul. 6-8, 1987, Pittsburgh, Pennsylvania, pp. 14-19, D. B. Johnson, et al., "Sender-Based Message Logging."
FTCS 19, Digest of Papers, Jun. 20-23, 1989, Chicago, Ill., pp. 184-190, N. A. Spiers, et al., "Using Passive Replicates Delta4 to Provide Dependable Distributed Computing."
Proceedings, 5th Symposium on Reliability in Distributed Software and Database Systems, pp. 207-219, P. S. Yu, et al., "Transaction Recovery in Distributed DB/DC Systems."

Primary Examiner—Robert W. Beausoliel, Jr.
Assistant Examiner—Ly V. Hua
Attorney, Agent, or Firm—Nathan Cass; Mark T. Starr

[57] ABSTRACT

A fault tolerant computer system which operates to automatically provide fault tolerant operation in a manner which reduces the frequency of checkpointing, while requiring neither simultaneity nor atomicity with respect to information transmitted to backups. These advantage are accomplished by providing operation such that message transmissions from primary tasks running on a data processor to external backups may be delayed until an action is performed which will persist after failure of the data processor. Although such operation may result in the backups hot having received all of the messages transmitted to their respective primary tasks when failure occurs, recovery is nevertheless obtained using the backups, since transmission to backups is controlled so that all backups agree on the state of the data processor at the time of failure, which need not be the actual state of the data processor at the time of failure.

23 Claims, 9 Drawing Sheets

FIG. 1 (PRIOR ART)

PARALLEL COMPUTER SYSTEM PCS

FIG. 2 (PRIOR ART)

TASK PROCESSOR XY

EXAMPLE 1

EXAMPLE 3

FIG. 7

EXAMPLE 3
(CONTINUED FROM FIG. 6)

EXAMPLE 5

FIG. 9

FAULT TOLERANT COMPUTER SYSTEM

BACKGROUND OF THE INVENTION

This invention relates to improved means and methods for providing fault tolerance in a data processing system.

As computer systems increase in speed, power and complexity, it has become of increasing importance to provide fault tolerance in such systems to prevent the system from "going-down" in the event of hardware and/or software failure. However, providing fault tolerant capabilities in a computer system has proven to be expensive as well as introducing significant performance penalties.

A basic way of achieving fault tolerance in a data processing system is to provide each task (also called a process) with a backup task such that, if the primary task fails, the backup task is automatically able to recover and continue execution. For example, a primary task and its backup task could be provided using a pair of simultaneously executing CPUs (central processing units) intercoupled such that, if one fails, execution continues on the other. It will be appreciated that the need to provide such duplicate hardware is a very expensive way of achieving fault tolerance, particularly since the simultaneously operating duplicate hardware cannot be used to provide additional data processing power.

One known approach for avoiding hardware duplication is to provide a first CPU for the primary task, and a second CPU for the backup task, the backup becoming active to recover and continue execution only if the primary fails. Until then, the backup CPU can do other processing. In order to assure that the backup process can take over in the event the primary process fails, this known approach provides for a checkpointing operation to occur whenever the primary data space changes. This checkpointing operation copies the primary's state and data space to that of the backup so that the backup task will be able to continue execution if the primary task fails. However, the frequent checkpointing required by this approach detrimentally affects performance and also uses up a significant portion of the added computing power.

Another known approach is disclosed in U.S. Pat. No. 4,590,554. Although this approach also uses checkpointing, it provides the advantage of employing a fault tolerant architecture which significantly reduces the frequency of checkpointing. However, the approach has the disadvantage of requiring a message transmission protocol which is essentially synchronous in that it requires messages to be transmitted to primary and back-up processors substantially simultaneously. Also, the disclosed approach in the aforementioned patent has the additional disadvantage of requiring atomic transmission, wherein transmittal of a message by a task is not allowed unless the receiving tasks and all backups indicate the are able to receive the message. Furthermore, no receiving task is allowed to proceed until all receiving tasks and backups have acknowledged receipt of the message. These message transmission protocol requirements introduce constraints that add complexity to the system, as well as having a significant detrimental effect on performance.

Similar approaches to that disclosed in the aforementioned patent U.S. Pat. No. 4,590,554 are described in an article by A. Borg, et al., "A Message System Supporting Fault Tolerance," Ninth Symposium on Operating Systems Principles (Breton Woods, N.H., Oct. 1983), Pages 90-99, ACM, New York, 1983, and in an article by A. Borg, et al., "Fault Tolerance Under UNIX," ACM Transactions on Computer Systems, Vol. 7, No. 1, February 1989, pages 1-24.

SUMMARY OF THE INVENTION

A broad object of the present invention is to provide improved means and methods for achieving fault tolerance in a data processing system.

Another object of the invention is to provide a fault tolerant data processing system having the advantages of the approach disclosed in the aforementioned U.S. Pat. No. 4,590,554, while reducing message transmission restraints so as to permit achieving significantly enhanced system performance.

A further object of the invention is to provide a fault tolerant data processing system in accordance with the foregoing objects, wherein fault tolerant operation occurs automatically and transparently with respect to both the programmer and the user.

In a particular preferred embodiment of the invention, the above objects are realized by providing a fault tolerant data processing system which reduces checkpointing while using a system organization and message transmission protocol which requires neither simultaneity nor atomicity, whereby enhanced performance is achieved.

The specific nature of the invention as well as other objects, features, advantages and uses thereof will become evident from the following detailed description of a preferred embodiment along with the accompanying drawings.

DETAILED DESCRIPTION

Like numeral and characters designate like elements throughout the figures of the drawings.

Summary of the Disclosed Embodiment of U.S. Pat. No. 4,590,554

It will be helpful in understanding the contribution of the present invention and the detailed description to be provided herein to initially summarize the construction and operation of the embodiment disclosed in the aforementioned U.S. Pat. No. 4,590,554, the contents of which are incorporated herein. For this purpose, reference is directed to FIGS. 1 and 2 herein which respectively correspond to FIGS. 1 and 2 of U.S. Pat. No. 4,590,554.

Figure 1:
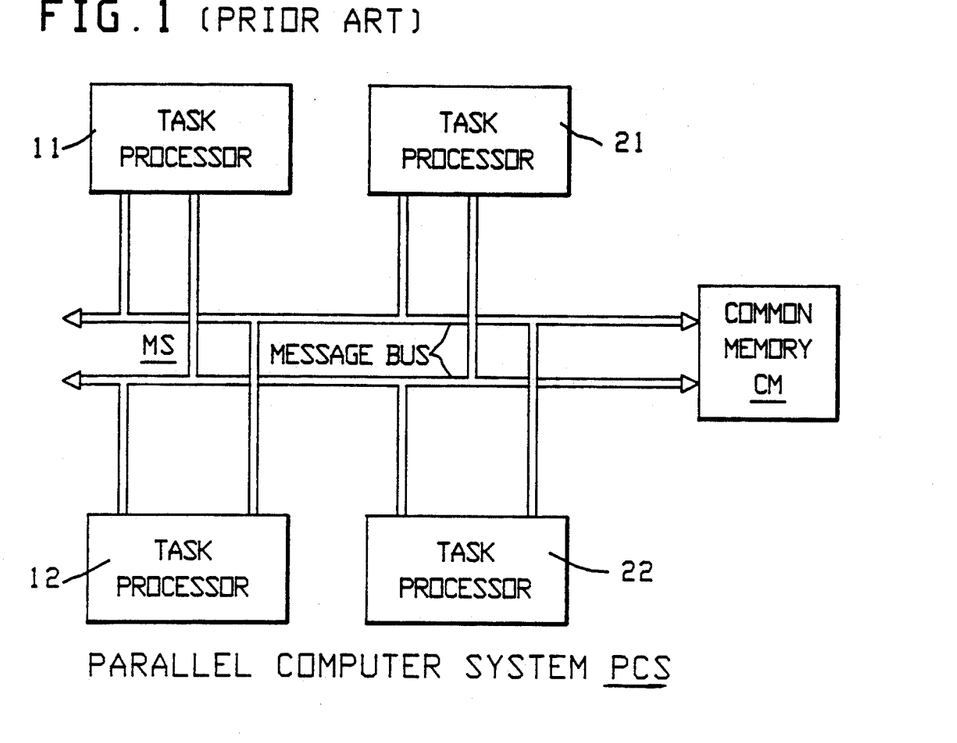
FIG. 1 is a block diagram of a prior art fault tolerant system taken from U.S. Pat. No. 4,590,554.

FIG. 1 illustrates a parallel computer system PCS comprised of primary processors 11 and 21, their respective associated backup processors 12 and 22, a common memory CM, and an interconnecting message bus MB.

Figure 2:
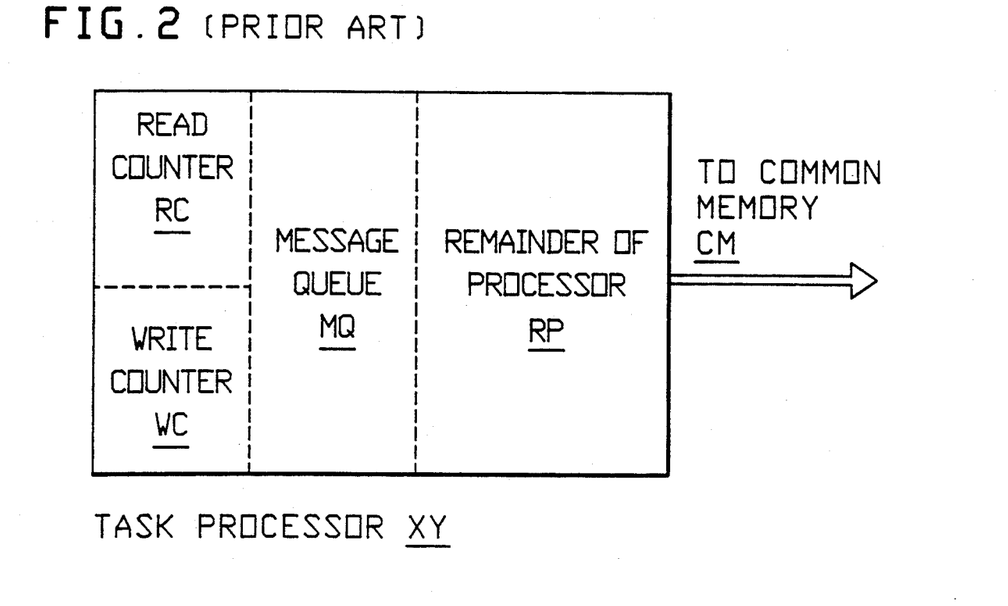
FIG. 2 is a generalized block diagram of one of the task processors in FIG. 1, also taken from U.S. Pat. No. 4,590,554.

FIG. 2 illustrates one of the processors in FIG. 1, and comprises a read counter RC, a write counter WC, a message queue MQ and the remainder of the processor RP. A primary processor (11 or 21) uses only the read counter RC, and a backup processor (12 or 22) uses only the write counter WC. Both RC and WC are initialized to zero at the start of operations. During operation, the read counter RC in each primary processor accumulates a count of the number of messages which its respective primary processor (11 or 21) reads from its message queue MQ to the remainder of the processor RP. The write counter WC in each backup processor (12 or 22) accumulates a count of the number of messages transmitted by its respective primary processor (11 or 21).

The operation described for the embodiment disclosed in U.S. Pat. No. 4,590,554 assumes that a first process (task) is being executed on primary processor 11 and a second process (task) is being executed on primary processor 21. Each message transmitted by a primary processor (e.g. 11) is sent substantially simultaneously to three processors, the destination primary processor (e.g. 21), the backup processor 22 of the destination processor 21, and the backup processor 12 of the transmitting processor 11. Only when all three processors have received the message and so acknowledged is the message transmission considered complete (atomicity). Both the destination processor 21 and its backup processor 22 load the message into their respective message queue MQ. However, the transmitting processor's backup processor 12 uses the received message merely to increment its write counter WC, the message thereafter being discarded. Each time a primary processor processes a received message, it increments its read counter by one.

Checkpointing is automatically initiated between primary and backup processors in the embodiment of U.S. Pat. No. 4,590,544 when the number of messages in the message MQ of a backup processor becomes too large. Checkpointing causes the backup process to be brought to the same state as its primary process, including making their data spaces identical. In addition, checkpointing causes the primary process to zero its read counter RC after sending the accumulated read count to its backup process. It will be remembered that this read count RC indicates the number of messages read by the primary process from its message queue MQ since the start or the last checkpointing. The backup process uses this read count during checkpointing to discard the same number of messages from its message queue MQ. Thus, if the primary process should fail, the backup process will not process messages already processed by the primary process.

As an example of the operation of the embodiment of aforementioned U.S. Pat. No. 4,590,544, it will be assumed that primary processor 21 fails. In such a case, its backup processor 22 will start from the point of the last checkpointing (or from the start), and begin processing the messages in its message queue MQ (FIG. 2). These are the same messages which were sent to the primary processor 21. In order to provide proper recovery, the backup processor 22 is prevented from retransmitting any messages that its failed primary processor 21 transmitted before failure. This is accomplished by using the accumulated count in the write counter WC of the backup processor 22, which it will be remembered corresponds to the number of messages sent by its respective primary processor 21. Each time an output message is produced by the backup processor 22 during recovery, this write counter WC is decremented by one. The backup processor 22 is allowed to transmit a message only after the write counter WC has reached zero. The backup processor 22 is thus brought up to the state of its failed primary processor 21 and can now take over processing of the process (task) which the failed primary processor 21 had been executing.

A Preferred Embodiment of the Present Invention

The preferred embodiment of the present invention takes advantage of a number of important insights considered below:

Insights

If a task receives a message, and then fails immediately, one may proceed as if the task failed before receiving the message.

In fact, one may choose to proceed as if the task failed before receiving the message until the task performs some action that will persist after the failure, for example, the task writes to a disk or terminal, or sends a message to another task that survives the failure. Since a CPU failure causes the failure of all tasks resident in that CPU, a message sent to another task running in the same CPU is not an action that will persist after a CPU failure, unless the receiver in turn performs a "persistent action".

More generally, if a CPU fails, it is important that all devices and tasks external to that CPU (other CPUs, disks, terminals, etc.) agree on the state of the CPU at the time of failure. It is not important whether the agreed upon state is the actual state of the CPU at the time of the failure.

The failed CPU may in fact have performed many additional processing steps, but no persistent actions, in which case the backups need not take them into account in order to recover properly. Recovery can thus commence at the agreed on state, and recompute the processing steps up to and beyond the actual state at the time of failure. In fact, recovery may perform different processing steps than the original CPU, but this is transparent to the user, as will be understood from the above insights, since no consequences of the original processing steps are visible.

DESCRIPTION OF PREFERRED EMBODIMENT

Figure 3:
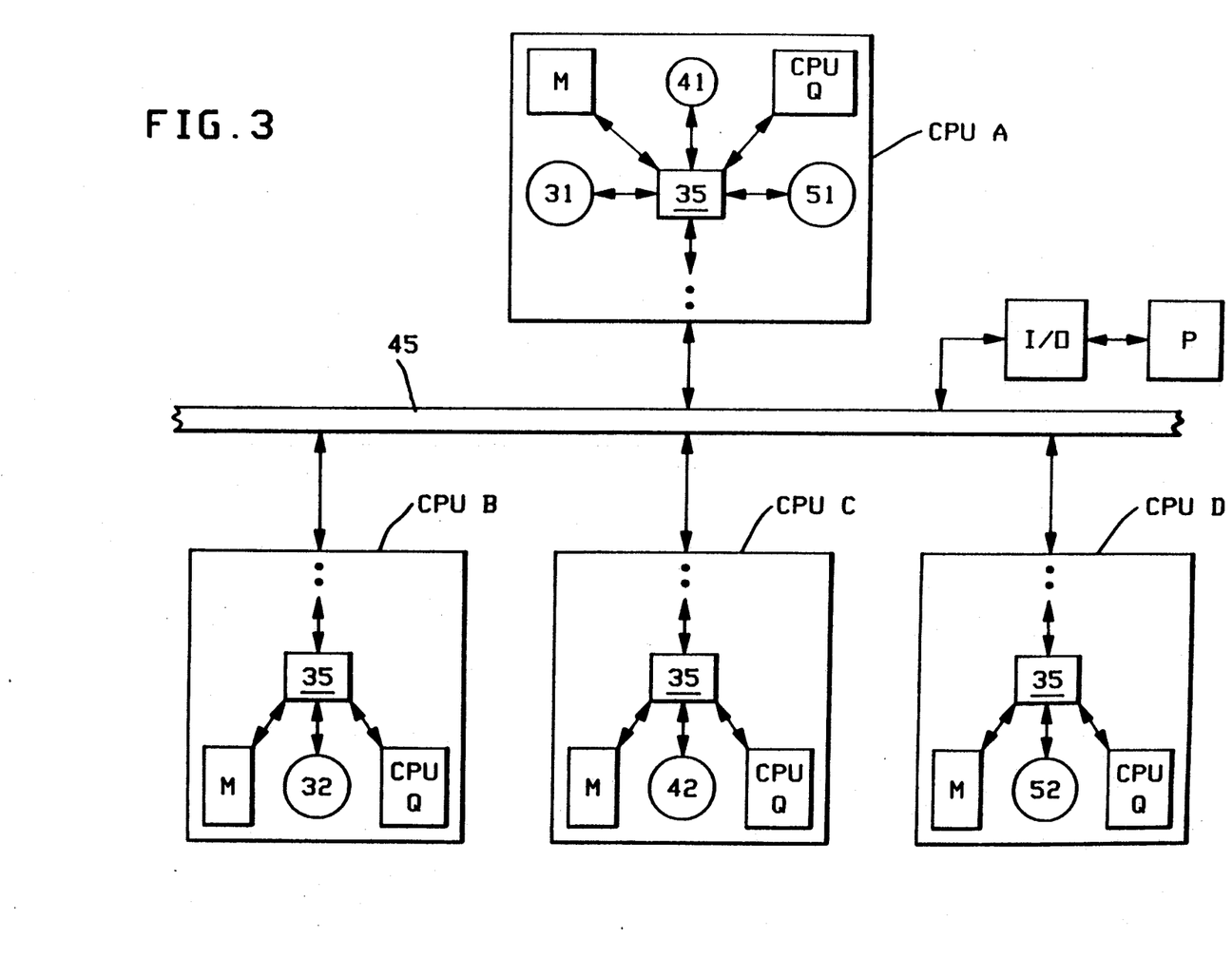
FIG. 3 is a block diagram of a preferred embodiment of a fault tolerant system in accordance with the invention.

The manner in which the present invention takes advantage of the above described insights will become evident from the following description of a preferred embodiment generally illustrated in FIG. 3.

As shown in FIG. 3, three primary tasks 31, 41, and 51 are implemented on CPU A, and communicate with each other and with an outgoing CPU Queue via an internal message network 35, which may be a conventional bus arrangement. Although only three primary tasks 31, 41, and 51 are illustrated on CPU A, it will be understood that additional tasks could be provided.

As also shown in FIG. 3, task 31 on CPU A is provided with a backup task 32 implemented on CPU B, task 41 on CPU A is provided with a backup task 42 implemented on CPU C, and task 51 on CPU A is provided with a backup task 52 implemented on CPU D. More than one backup task could be implemented on the same CPU. Each CPU includes a memory M coupled to the internal communication network 35 which provides a respective data space for each task implemented on the CPU. CPU's B,C, and D may each have a CPU Queue (as does CPU A), but it is not used if the CPU contains only backup tasks. Communication between CPUs A,B,C and D is provided by an external communication network 45 which may take various forms known in the art, such as indicated by the message BUS MB in the aforementioned U.S. Pat. No. 4,590,544. As shown in FIG. 3, peripherals P are also coupled to the external communication network 45 via an I/O. The peripheral P may, for example, include one or more disk drives.

Each of the primary tasks 31,41,51 and their respective backup tasks 32,42,52 will now be considered in more detail. Although only a particular arrangement is illustrated in FIG. 3, the invention is not to be considered as limited thereto, since one skilled in the art will understand from the description herein how the present invention can be used in different arrangements and with additional tasks and CPUs. For the purposes of the preferred embodiment being considered herein, it will be assumed that primary tasks 31,41,51 which are all on CPU A, receive messages only from each other, via internal communication network 35, and not from outside of their respective CPU A. It will also be assumed that message deliveries from tasks 31,41,51 outside of CPU A are only to their respective backup tasks 32,42,52 on CPUs B,C,D respectively, via external communication network 45. As will be evident to those skilled in the art, the structure and operations described herein for a task are implemented by its respective CPU.

Figure 3A:
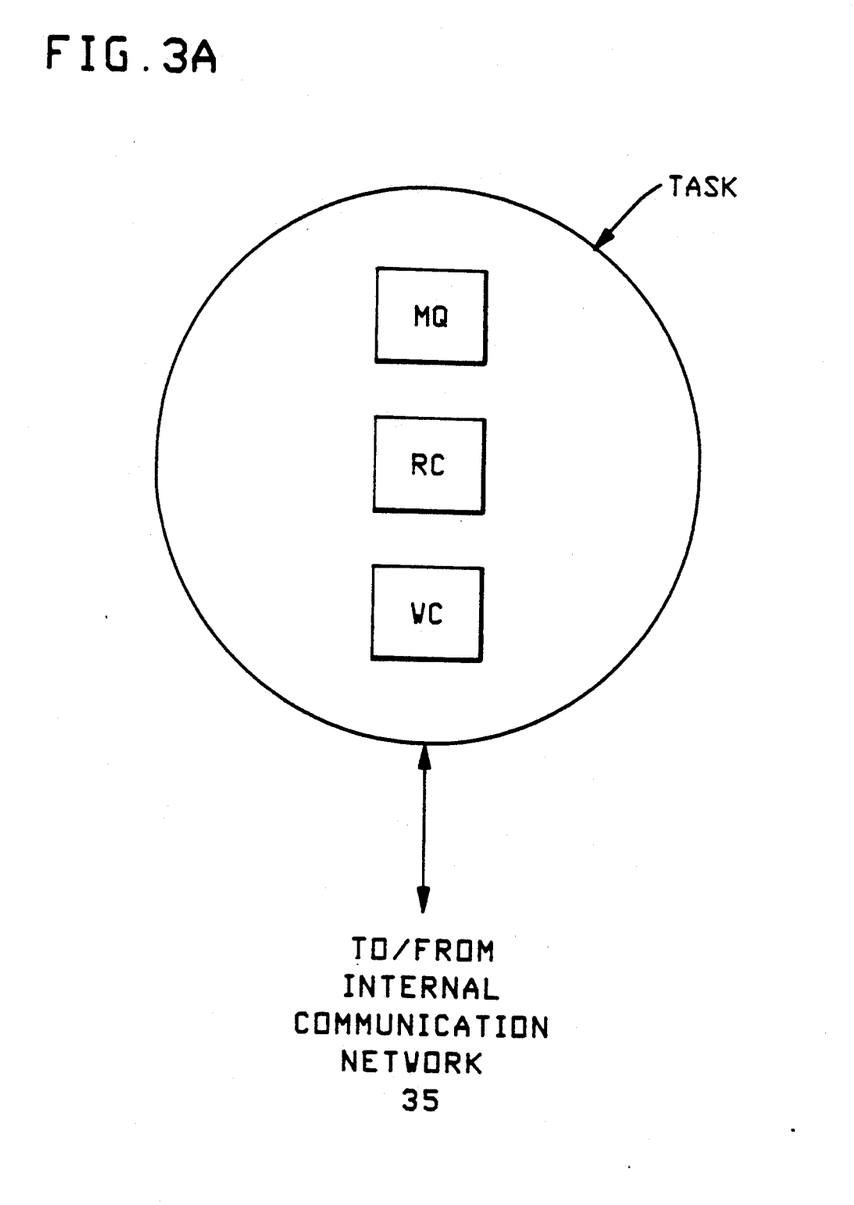
FIG. 3A is a generalized representation of a task in FIG. 3.

As shown in FIG. 3A, each task (31,32,41,42,51,52 in FIG. 3) includes a message queue MQ for receiving and storing messages. Each task also includes a read counter RC and a write counter WC. If the task is a primary task (such as 31,41,51 in FIG. 3), then only the read counter RC is used, this use being to accumulate a count of the number of messages read by the primary task from its message queue MQ. If, on the other hand, the task is a backup task (such as 32,42, and 52 in FIG. 3), then only the write counter WC is used, this use being to accumulate a count of the messages sent by its respective primary task (31,41,51 in FIG. 3).

The operation of the message queue MQ, read counter RC and write counter WC may typically be as previously described herein with respect to the aforementioned U.S. Pat. No. 4,590,554. Also, checkpointing and recovery by a backup task may likewise typically be provided as described in aforementioned U.S. Pat. No. 4,590,554, except for the differences pointed out herein resulting from taking advantage of the previously considered "insights."

The operation of the preferred embodiment illustrated in FIGS. 3 and 3A will now be considered in more detail. As mentioned previously, it is assumed for the preferred embodiment being described that primary tasks 31,41,51 on CPU A communicate only with each other, via internal communication network 35, and that respective backup tasks 32 are provided on CPUs B,C, and D, respectively. Each message sent by a primary task (31,41, or 51) typically includes an associated task address which is used by the internal communication network 35 to direct the message to the indicated task. Messages required to be sent to backup tasks (32,42,52 on CPUs B,C,D, respectively) are sent by the internal communication network 35 to the outgoing CPU Queue, which operates in a first-in, first-out (FIFO) manner.

An important feature of the present invention is that, by taking advantage of the insights considered earlier herein, a primary task which transmits a message to another task on the same CPU is allowed to continue its processing immediately, so long as delivery of the message to this other task and the respective CPU Queue are assured, even though corresponding backup messages in the CPU Queue have not been sent to the backup tasks, thereby providing high speed processing. Unlike in the aforementioned U.S. Pat. No. 4,590,544, these backup messages can be sent to the appropriate backup tasks via the external communication network 45 when convenient to do so. This applies so long as a primary task does not perform a persistent action. It will be remembered that a persistent action is an action taken by a primary task which will persist after failure, such as when the task writes to a disk or terminal, or sends a message to another task that survives the failure.

When a primary task (21 or 31) is required to perform a persistent action, the primary task first checks the outgoing CPU Queue to determine whether all backup messages corresponding to messages already processed by the task have been delivered to the backups. If the delivery of all such required messages has been assured, the task performs the persistent action and continues processing. If not, the primary task initiates the required delivery to the backups, after which the primary task then performs the persistent action and continues processing. The task may again continue processing without being concerned about delivery of processed messages to their backups until the next persistent action is required to be performed. It will be understood that various techniques well known in the art may be employed for assuring the delivery of a transmitted message, such as for example, by using acknowledgment signals, handshaking, echos, error checking, or other appropriate means.

Examples of typical operations

In order to permit the present invention to be clearly understood, examples (along with state tables) illustrative of operations of the preferred embodiment of FIG. 3 will next be presented. These examples are presented in summarized form in the flow charts provided in FIGS. 4-9. These flow charts also indicate the point in the flow corresponding to the state tables included for each example. Additionally, it will be helpful in understanding the contributions of the present invention to compare these examples and tables to those presented in the aforementioned U.S. Pat. No. 4,590,554.

The examples presented below involve only primary tasks 31 and 41 on CPU A, and respective backup tasks 32 and 42 on CPU B and CPU C, respectively. Accordingly, only these tasks and CPUs are referred to in these examples. In addition, since only CPU A need have a CPU Queue for these examples, references to a CPU Queue refer to the CPU Queue of CPU A. In addition, it is assumed that appropriate provision is made for assuring the delivery of transmitted messages, as indicated above.

Figure 4:
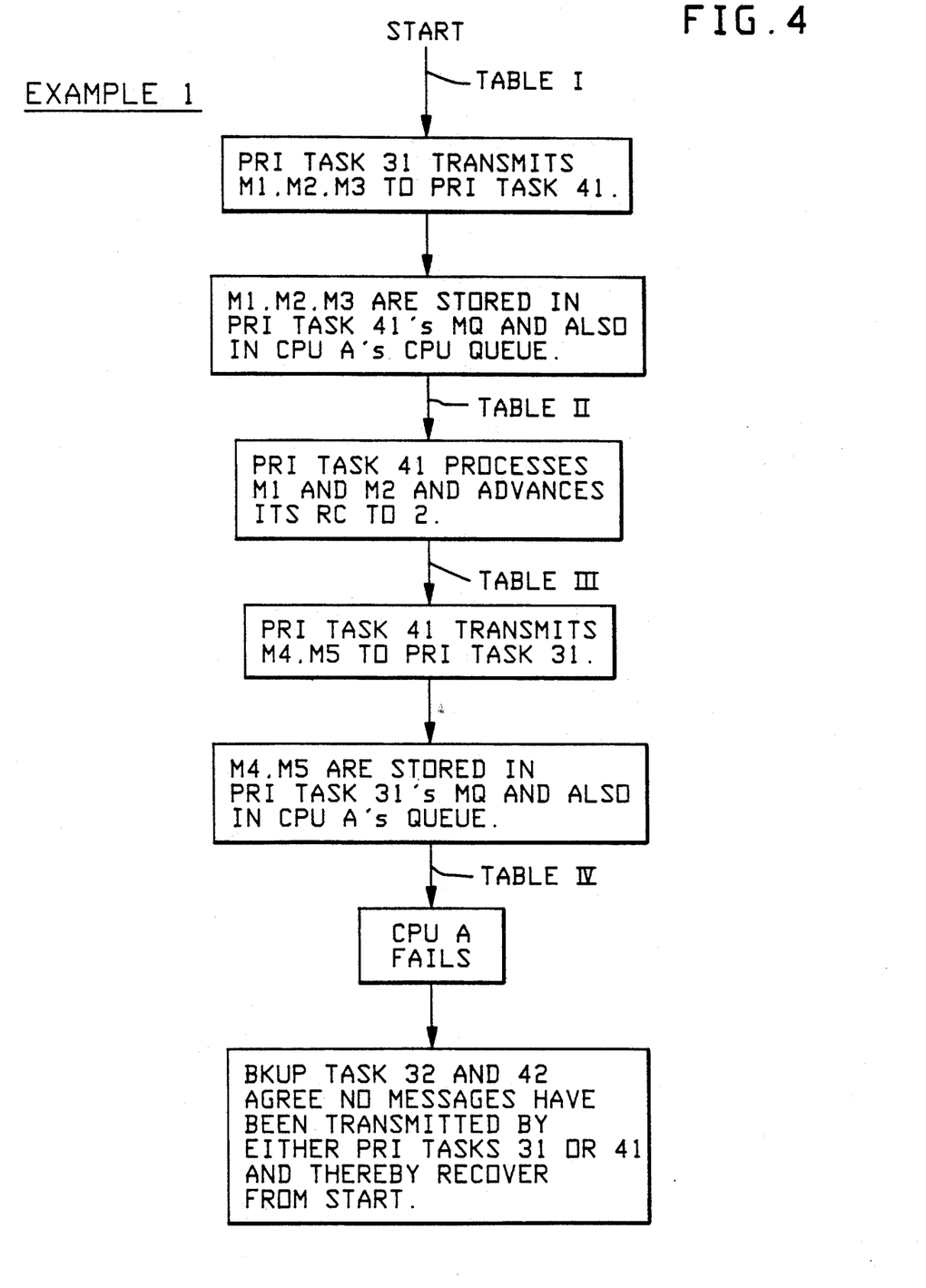
FIGS. 4-9 are flow charts illustrating various operating examples for the preferred embodiment of FIG. 3.

Example 1 (FIG. 4)

TABLE I below shows the start state of the write counter WC, the read counter RC, the message queue MQ and the CPU Queue for primary tasks 31,41, on CPU A, and their respective backup tasks 32,42 on CPUs B and C, respectively.

TABLE I

| | (Example 1, FIG. 4): | | | |
|---|---|---|---|---|
| Task/CPU | Write Counter WC | Read Counter RC | Message Queue MQ | CPU-Queue |
| 31/A | unused | 0 | empty | empty |
| 32/B | 0 | unused | empty | |
| 41/A | unused | 0 | empty | |
| 42/C | 0 | unused | empty | |

Assume that primary task 31 transmits three messages M1,M2,M3 to primary task 41, which are stored in task 41's message queue MQ. These messages are also stored in the CPU Q for later delivery to backup CPUs B and C. Task 31 may continue its processing even though messages M1,M2,M3 are not transmitted to backup CPUs B and C which contain backup tasks 32 and 42, respectively. CPU A may transmit messages M1,M2,M3 at its leisure so long as no persistent action is required by primary tasks 31 or 41. For this example, it is assumed that CPU A does not transmit these messages M1,M2,M3 at this time. The result is shown in TABLE II below:

TABLE II

| | (Example 1, FIG. 4): | | | |
|---|---|---|---|---|
| Task/CPU | Write Counter WC | Read Counter RC | Message Queue MQ | CPU Queue |
| 31/A | unused | 0 | empty | M1,M2,M3 |
| 32/B | 0 | unused | empty | |
| 41/A | unused | 0 | M1,M2,M3 | |
| 42/C | 0 | unused | empty | |

Next, task 41 reads M1 and M2 stored in its message MQ, processes them, and advances its read counter RC to two to indicate that two messages have been processed. The result is shown in TABLE III below:

TABLE III

| | (Example 1, FIG. 4): | | | |
|---|---|---|---|---|
| Task/CPU | Write Counter WC | Read Counter RC | Message Queue MQ | CPU Queue |
| 31/A | unused | 0 | empty | M1,M2,M3 |
| 32/B | 0 | unused | empty | |
| 41/A | unused | 2 | M3 | |
| 42/C | 0 | unused | empty | |

In response to messages M1 and M2, task 41 generates two messages M4 and M5, and sends them to task 31. Messages M4 and M5 are stored in task 31's message queue MQ and are also stored in the CPU Queue for later delivery to CPUs B and C. The result is shown in TABLE IV below:

TABLE IV

| | (Example 1, FIG. 4): | | | |
|---|---|---|---|---|
| Task/CPU | Write Counter WC | Read Counter RC | Message Queue MQ | CPU Queue |
| 31/A | unused | 0 | M4,M5 | M1,M2,M3,M4,M5 |
| 32/B | 0 | unused | empty | |
| 41/A | unused | 2 | M3 | |
| 42/C | 0 | unused | empty | |

Assume that CPU A fails at this point, taking down primary tasks 31 and 41. Backup tasks 32 and 42 agree CPU A was in a state such that no messages were sent or processed by primary tasks 31 and 41 (since none were sent by the CPU Queue of CPU A). Backup tasks 32 and 42 thus replay based on this agreed on state, starting from the last known state, which is the initial state. Thus, the entire processing up to this point is correctly repeated from the initial state by backup tasks 32 and 42 which communicate with each other via external communication network 45. Note that successful recovery is achieved even though the state of CPU A prior to its failure (TABLE IV) was in fact very different from that agreed to by backup tasks 32 and 42.

Figure 5:
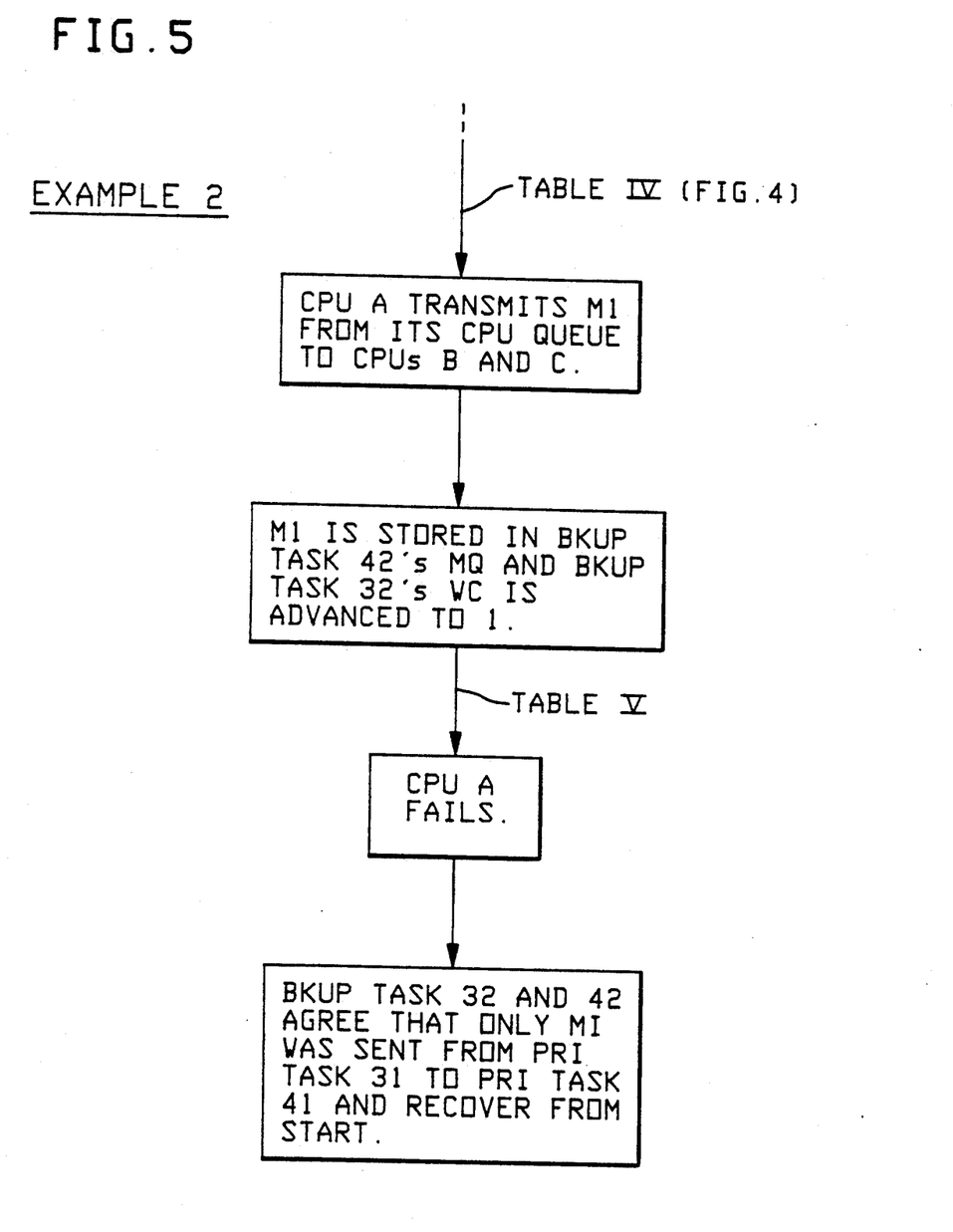

Example 2 (FIG. 5)

The beginning state of this example is represented by TABLE IV from example 1 above, which shows the state prior to CPU A's failure. This Example 2 assumes that CPU A transmits message M1 in its CPU Queue to backup tasks 32 and 42 on CPUs B and C respectively, before CPU A fails. Message M1 is thus stored in backup task 42's message Queue MQ and backup task 31's write counter WC is advanced to one to indicate one message sent by its respective primary task 41. The result of this transmission by CPU A V is shown in TABLE V below:

TABLE V

| | (Example 2, FIG. 5): | | | |
|---|---|---|---|---|
| Task/CPU | Write Counter WC | Read Counter RC | Message Queue MQ | CPU Queue |
| 31/A | unused | 0 | M4,M5 | M2,M3,M4,M5 |
| 32/B | 1 | unused | empty | |
| 41/A | unused | 2 | M3 | |
| 42/C | 0 | unused | M1 | |

If CPU A now fails, backup tasks 32 and 42 both agree that CPU A was in a state where only M1 had been sent by primary task 31 to primary task 41. Recovery by backup tasks 32 and 42 is thus performed based on this agreement with tasks 32 and 42 restarting from the last known state (the initial state). This recovery may typically be provided as described in connection with the aforementioned U.S. Pat. No. 4,590,554. It will thus be understood that, when task 32 regenerates M1 during recovery, its write counter WC (which is at 1 as shown in TABLE V above), is decremented by one to zero, and M1 is discarded. When M2 and M3 are regenerated by backup task 32, they are transmitted normally to task 42 via the external communication network 45, since task 32's write counter WC is now zero. When task 42 restarts and attempts to process its first message, it is given the original message M1, stored in its message queue MQ (TABLE V above). Since message queue MQ is now empty, further message reads by backup task 42 use the regenerated M2 and M3 transmitted from recovering backup task 32.

Figure 6:
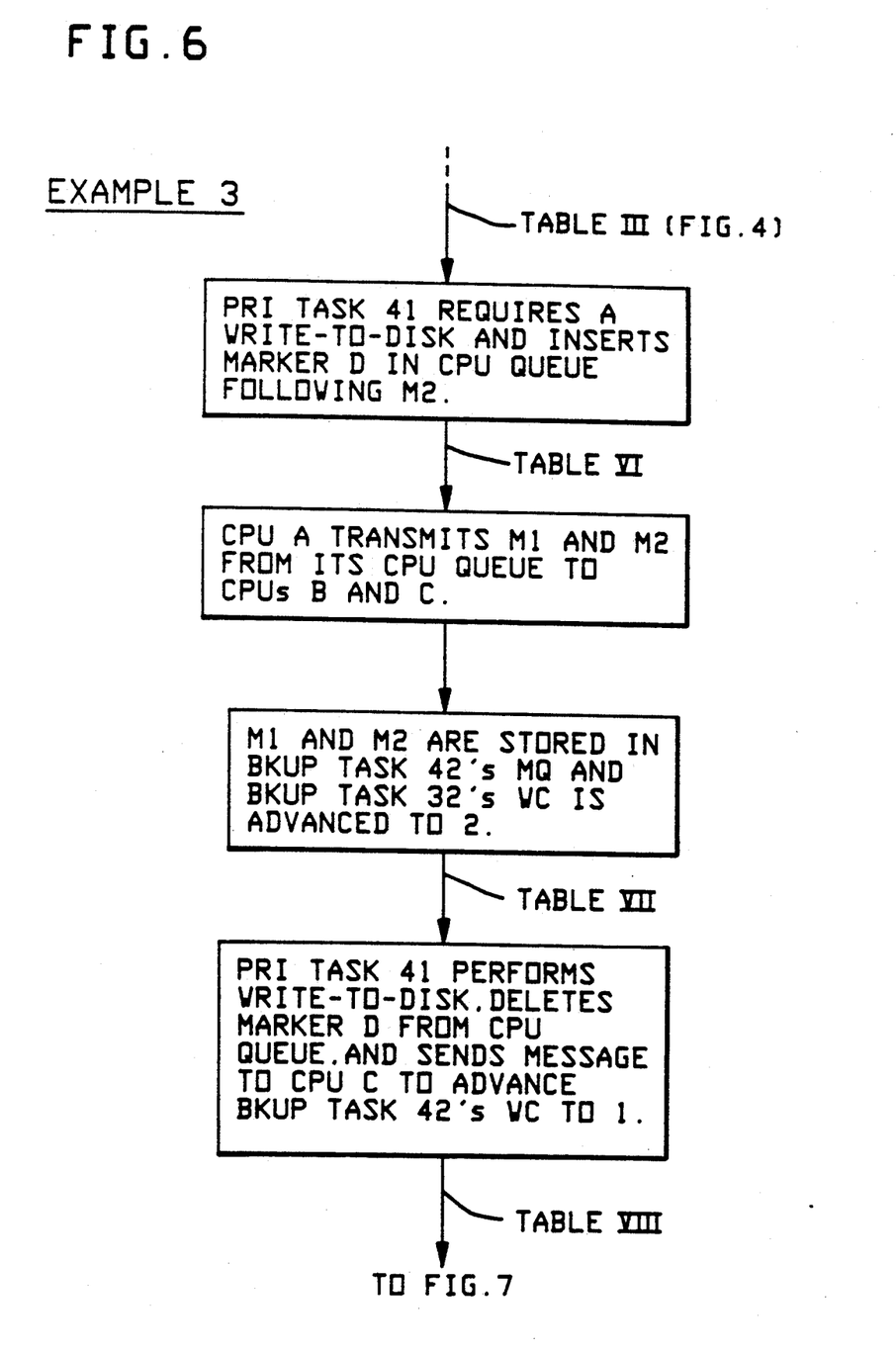

Example 3 (FIG. 6)

The beginning state of this example is shown by TABLE III from Example 1 above. This Example 3 assumes that task 41 needs to perform a persistent action at this time, such as a write-to-disk (this disk may typically be located in peripheral P in FIG. 3). Before the disk is written, all messages processed in CPU A must be transmitted to their respective backup tasks. Thus, messages M1 and M2 (which have been processed) must be transmitted to CPUs B and C containing backup tasks 32 and 42 before the write-to-disk, since M1 and M2 have been processed (by task 41). To insure that messages M1 and M2 are sent before the write-to-disk is performed) a marker D is stored in the CPU Queue at a position at least after M1 and M2 so that D is not reached for performance until after M1 and M2 have been sent. The result of storing D in the CPU Queue is shown in TABLE VI below:

TABLE VI (Example 3, FIG. 6):

| Task/CPU | Write Counter WC | Read Counter RC | Message Queue MQ | CPU Queue |
|---|---|---|---|---|
| 31/A | unused | 0 | empty | M1,M2,D,M3 |
| 32/B | 0 | unused | empty | |
| 41/A | unused | 2 | M3 | |
| 42/C | 0 | unused | empty | |

Note with respect to TABLE VI above that D could be placed in the CPU Queue at any point after M1 and M2, (for example, after M3) since sending M3 along with M1 and M2 will not interfere with recovery.

In order to permit primary task 41 to perform the write-to-disk, CPU A now transmits M1 and M2 from its CPU Queue to CPUs B and C. Messages M1 and M2 are thus stored in the message queue MQ of backup task 42 on CPU C, and the write counter WC of backup task 32 is advanced to 2 to indicate that two messages (M1 and M2) have been sent by its respective primary task 31 on CPU A. The result is shown in TABLE VII below:

TABLE VII (Example 3, FIG. 6):

| Task/CPU | Write Counter WC | Read Counter RC | Message Queue MQ | CPU Queue |
|---|---|---|---|---|
| 31/A | unused | 0 | empty | D,M3 |
| 32/B | 2 | unused | empty | |
| 41/A | unused | 2 | M3 | |
| 42/C | 0 | unused | M1,M2 | |

Task 41 now deletes the D entry form CPU A's queue, and performs the write-to-disk.

In order to prevent task 41's backup task 42 on CPU form repeating the write-to-disk if CPU A should fail, the performance of the write-to-disk by primary task 41 also results in a message being sent to CPU C which causes backup task 42's write counter WC to be advanced to 1. The result is shown in TABLE VIII below:

TABLE VIII (Example 3, FIGS. 6 and 7):

| Task/CPU | Write Counter WC | Read Counter RC | Message Queue MQ | CPU Queue |
|---|---|---|---|---|
| 31/A | unused | 0 | empty | M3 |
| 32/B | 2 | unused | empty | |
| 41/A | unused | 2 | M3 | |
| 42/C | 1 | unused | M1,M2 | |

Figure 7:
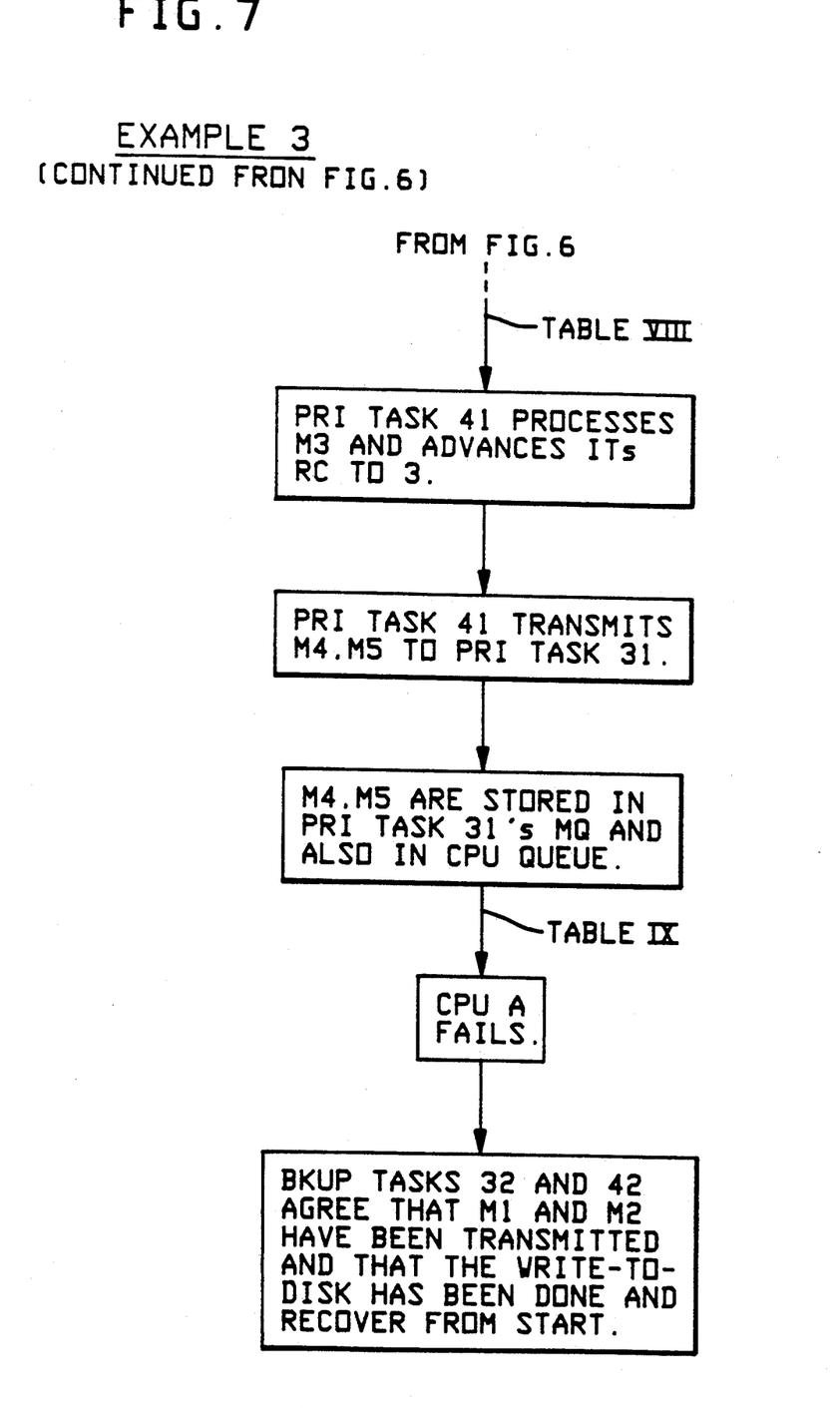

Assume that task 41 next reads M3 from its message queue MQ, processes M3, and then replies by sending messages M4 and M5 to task 31, which are stored in task 31's message queue MQ and also in the CPU Queue. The result is shown in TABLE IX below:

TABLE IX (Example 3, FIG. 7):

| Task/CPU | Write Counter WC | Read Counter RC | Message Queue MQ | CPU Queue |
|---|---|---|---|---|
| 31/A | unused | 0 | M4,M5 | M3,M4,M5 |
| 32/B | 2 | unused | empty | |
| 41/A | unused | 3 | empty | |
| 42/C | 1 | unused | M1,M2 | |

If CPU A fails at this point (TABLE IX above), both CPUs B and C agree with respect to CPU A that MESSAGES M1 and M2 have been sent, and that the write-to-disk is done. The fact that task 41 processed M3 and sent M4 and M5 to task 31 before the failure is irrelevant to satisfactory recovery since no further persistent action occurred prior to CPU's failure. Recovery thus proceeds normally in the manner previously described. Since no checkpointing has yet occcured, recovery starts from the initial state (TABLE I). More specifically, with respect to backup task 32, messages M1 and M2 generated by task 41 during recovery are not sent but discarded, since write counter WC will not have decremented to "0" until after M2 is regenerated. With respect to backup task 42, messages M1 and M2 in its message queue MQ will be processed as occurred for the primary task 41 in now failed CPU A. When recovering backup task 41 reaches the point at which the write-to-disk is to be performed (which it will be remembered was performed by primary task 41), this write-to-disk operation is prevented from being performed again as a result of task 42's write counter WC being "1" at this time. It is only after task 42's write counter is decremented to "0" (following this disk-to-write prevention) that messages are sent by task 42. Accordingly since WC will thus be "0" when messages M4 and M5 are generated by task 42, they will be sent to task 32, thereby achieving recovery to the point reached prior to CPU A's failure. Processing then continues beyond the recovery point using backup tasks 32 and 42 communicating via external communications network 45.

Figure 8:
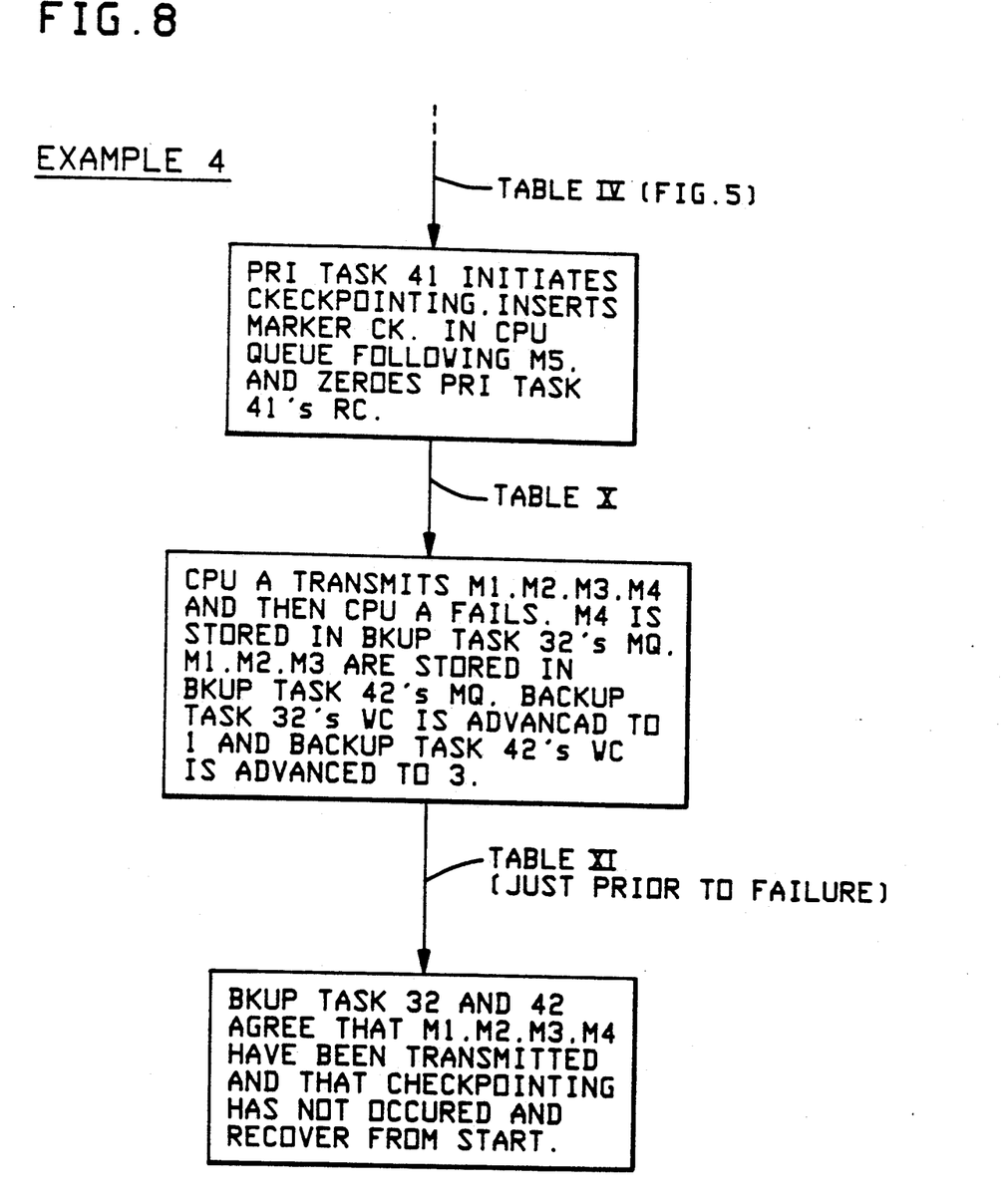

Example 4 (FIG. 8)

The purpose of this Example 4 (and Example 5) is to demonstrate checkpointing in the embodiment of FIG. 3, and assumes a beginning state corresponding to TABLE IV from Example 1 above.

Assume that, after reaching the state shown in TABLE IV above, task 41 initiates a checkpointing operation. This is a persistent action, since checkpointing requires that state information about task 41 be transmitted outside of CPU A. Accordingly, task 41 places the checkpointing data (or an appropriate checkpointing marker CK) in the CPU Queue at a position at least after M1 and M2, since they have been processed. The result is shown in TABLE X below:

TABLE X (Example 4, FIG. 8):

| Task/CPU | Write Counter WC | Read Counter RC | Message Queue MQ | CPU Queue |
|---|---|---|---|---|
| 31/A | unused | 0 | M4,M5 | M1,M2,M3, M4,M5,CK |
| 32/B | 0 | unused | empty | |
| 41/A | unused | 0 | M3 | |

TABLE X-continued (Example 4, FIG. 8):

| Task/CPU | Write Counter WC | Read Counter RC | Message Queue MQ | CPU Queue |
|---|---|---|---|---|
| 42/C | 0 | unused | empty | |

Note in TABLE X above that task 41's read counter RC has been zeroes since, as far as task 41 is concerned, the required checkpointing has already occurred. Also note that both tasks 31 and 41 can proceed with processing without concern as to when the checkpointing data is actually sent to its backup task 42 in CPU C, so long as any subsequently occurring persistent actions are delayed until after the checkpoint data is transmitted to its respective backup. Also note in TABLE X that CK was placed in the CPU Queue after M5, rather than directly after M1 and M2, which means that M3,M4 and M5 as well as M1 and M2 will be transmitted before the checkpointing data CK. This will not cause any problem, since CPU A is able to transmit messages from its CPU Queue at its convenience (as mentioned earlier), unless a persistent action is encountered, in which case processed messages have to be transmitted to their respective backups before the persistent action can be performed.

Assume for the purposes of Example 4 that CPU A now begins to transmit M1 through M5 to backup tasks 32 and 42 and 42 on CPUs B and C, respectively, but that CPU A fails after successfully transmitting M1,M2,M3,M4 so that neither M5 nor the checkpointing data CK are transmitted. The resulting state just prior to failure is shown in TABLE XI below:

TABLE XI (Example 4, FIG. 8):

| Task/CPU | Write Counter WC | Read Counter RC | Message Queue MQ | CPU Queue |
|---|---|---|---|---|
| 31/A | unused | 0 | M4,M5 | M5,CK |
| 32/B | 3 | unused | M4 | |
| 41/A | unused | 0 | M3 | |
| 42/C | 1 | unused | M1,M2,M3 | |

Backup tasks 32 and 42 on CPUs B and C, respectively, initiate recovery from the initial state (TABLE I) based on their agreed on perceptions that only messages M1,M2,M3,M4 were transmitted, and that checkpointing has not yet occurred.

Figure 9:
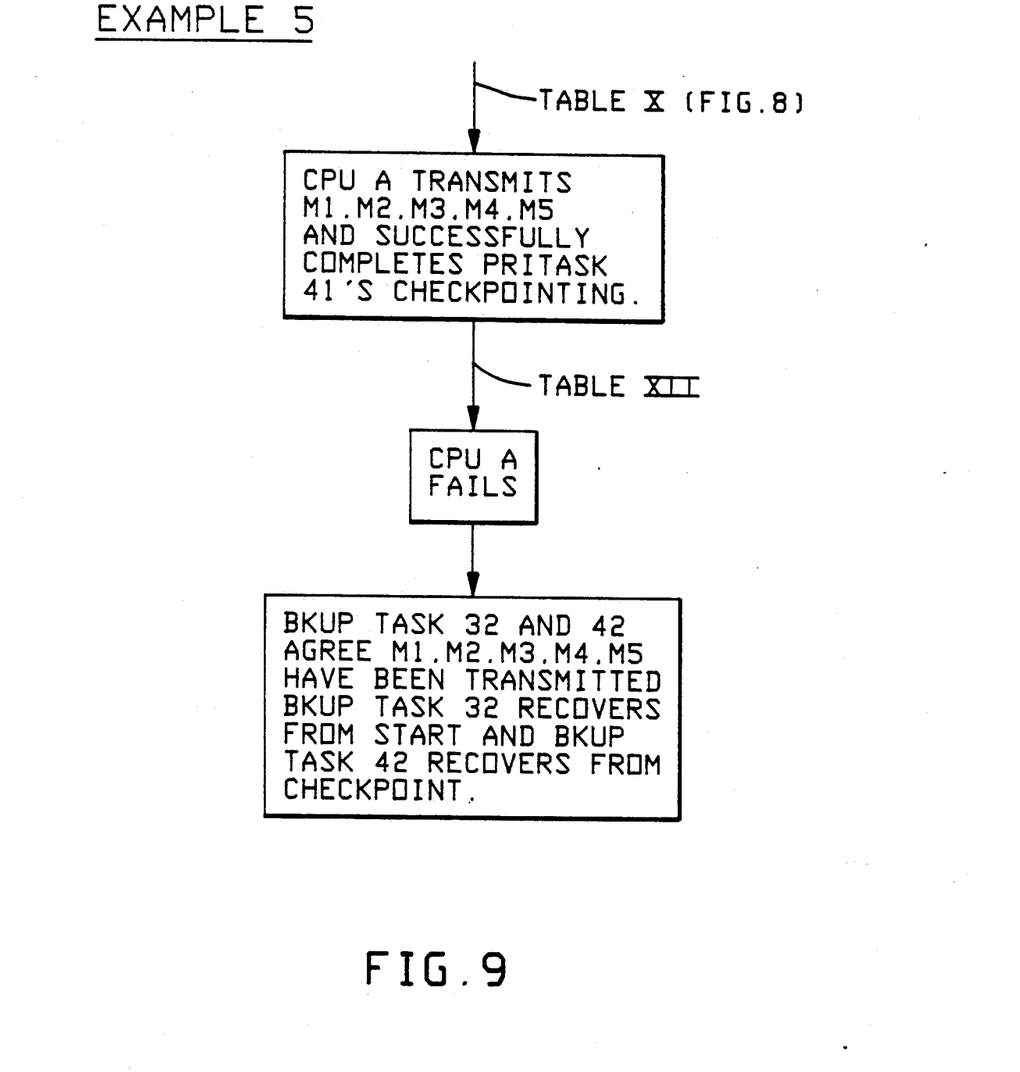

Example 5 (FIG. 9)

This Example assumes an initial state corresponding to TABLE X of Example 4 above. However, instead of failing after transmitting M1-M4, as described in Example 4, this Example 5 assumes that CPU A's transmission of M1-M5 and CK is successful, resulting in TABLE XII below:

TABLE XII (Example 5, FIG. 9):

| Task/CPU | Write Counter WC | Read Counter RC | Message Queue MQ | CPU Queue |
|---|---|---|---|---|
| 31/A | unused | 0 | M4,M5 | empty |
| 32/B | 3 | unused | M4,M5 | |
| 41/A | unused | 0 | M3 | |
| 42/C | 0 | unused | M3 | |

As will be remembered from the previous discussion, checkpointing brings the backup task 42 to the same state as its primary task 41, as well as making their data spaces identical in their respective memories M.

It will be understood that while messages M1 through M5 and CK are being transmitted, CPU A is free to continue processing further work for primary tasks 31 and 41, provided that further persistent actions are delayed until after the checkpointing data has been successfully transmitted.

If a failure of CPU A should subsequently occur, backup task 32 will recover from START and backup task 42 will recover from the above checkpoint.

While the invention has been described herein with respect to a particular preferred embodiment, it will be understood that a wide variety of modifications and extensions in construction, arrangement, and use are possible within the scope of the invention, and the claims following should be interpreted accordingly.

What is claimed is:

1. In a fault tolerant computer system including a first data processor and a second data processor, wherein said first data processor provides first and second primary tasks, and wherein said second data processor provides a backup task for backing up said second primary task on said first data processor, a method comprising:
   transmitting messages from said first primary task to said second primary task for processing thereby;
   allowing said second primary task to process received messages from said first primary task without transmitting said received messages to said backup task on said second processor so long as said second primary task does not perform a persistent action;
   transmitting at least messages processed by said second primary task to said backup task prior to the performance of a persistent action thereby; and
   providing for recovery of said second primary task in the event of failure thereof using said backup task and the messages transmitted thereto.

2. The method in accordance with claim 1, wherein said first primary task is provided with a backup task on a different data processor from said first data processor, and wherein said method also includes:
   transmitting messages form said second primary task to said first primary task for processing thereby;
   allowing said first primary task to process received messages from said second primary task without transmitting said received messages to the backup task of said first primary task so long as said first primary task does not perform a persistent action;
   transmitting at least messages processed by said first primary task to the backup task of said first primary task prior to the performance of a persistent action thereby; and
   providing for recovery of said first primary task in the event of failure thereof using a respective backup task and the messages transmitted thereto.

3. In a fault tolerant computer system including a data processor providing at least one task which performs a persistent action, a method comprising:
   providing a backup task external to said data processor for backing up said one task,
   transmitting messages to said one task;
   storing messages transmitted to said one task;
   transmitting stored messages to said backup task subsequently to said storing in a manner such that at least particular messages which have been processed by said one task are transmitted to said backup task prior to performance of said persistent action;

said one task continuing to process messages transmitted thereto concurrently with said transmitting of stored messages to said backup task; and in the event of failure of said one task, causing said backup task to process said messages transmitted thereto.

4. The method of claim 3, wherein the step of storing includes storing messages transmitted to said one task in a queue of said data processor, and wherein the step of transmitting stored messages to said backup task prior to performing said persistent action includes transmitting at least processed messages in said queue to said backup task prior to said persistent action.

5. The method of claim 4, including counting the number of messages processed by said one task.

6. The method of claim 3, including providing for the performance of a second task, and transmitting and storing a message form said one task to said second task.

7. The method of claim 6, including transmitting to said backup task the stored message transmitted from said one task to said second task prior to performance of said persistent operation if said stored message has been processed by said second task.

8. The method of claim 7, including said backup task providing a count of the number of messages transmitted by said one task.

9. The method of claim 8, wherein during processing by said backup task said count is used to determine when a message is to be transmitted by said backup task.

10. The method of claim 3, including performing a checkpointing operation between said one task and said backup task after at least a plurality of messages have been transmitted to said one task, said checkpointing operation including storing checkpointing data corresponding to the state of said one task, and transmitting said checkpointing data to said backup task at a time which is no later than required by the transmitting of processed messages to said backup task, said checkpointing data causing said backup task to be brought to the same state as said one task at the time of checkpointing.

11. The method of claim 10, wherein said checkpointing data includes a count of the number of messages processed by said one task since the start or last checkpointing thereof, and wherein said backup task uses said count for discarding a corresponding number of said messages sent thereto.

12. In a fault tolerant computer system including a data processor providing a plurality of primary tasks, at least one of said primary tasks performing a persistent action, a method comprising:

providing a corresponding plurality of interconnected backup tasks external to said data processor for backing up said plurality of primary tasks, the method comprising:

transmitting messages between said primary tasks for processing thereby;

storing the transmitted messages;

each primary task processing the messages transmitted thereto;

transmitting at least particular ones of the stored messages to said backup tasks subsequently to said storing in a manner such that there is transmitted to said backup tasks, prior to the performance of a persistent action, at least particular messages required for said backup tasks to recover form a failure of said data processor;

said primary tasks continuing to process messages transmitted thereto so long as the aforementioned transmitting of messages to said backup tasks is met; and recovering from said failure by causing said backup tasks to process the messages transmitted thereto.

13. The method of claim 12, wherein said particular messages are chosen such that said backup tasks and other parts of said system will agree on a particular state of each primary task prior to said failure which need not be the actual state thereof at the time of failure.

14. The method of claim 13, wherein said recovering includes causing said backup tasks to process the messages transmitted thereto in a manner which will result in each backup task arriving at a respective particular state.

15. The method of claim 13, including performing a checkpointing operation between a primary task and a respective backup task after at least a plurality of message have been transmitted to said primary task, said checkpointing operation including storing checkpointing data corresponding to the state of the primary task, and transmitting said checkpointing data to the respective backup task subsequently to said storing and at a time no later than required for said backup tasks to recover from failure of said data processor using the messages transmitted thereto from respective primary tasks, said checkpointing data causing the backup task to which said checkpointing data was transmitted to be brought to the same state as the respective primary task at the time of checkpointing.

16. The method of claim 15, wherein said primary tasks sequentially process messages transmitted thereto, wherein said storing of transmitted messages is in a queue which stores transmitted messages in the order of transmission, wherein said queue also stores a checkpointing indication at a position indicative of the time of performance of said checkpointing operation, wherein the performance of a persistent action is indicated in said queue by storing a persistent action indication positioned in said queue based on the position of the most recently processed message, and wherein said particular messages are chosen to be transmitted to said backup tasks prior to the performance of said persistent action if positioned earlier in said queue than said persistent action indication, and wherein said checkpointing data is also transmitted to the respective backup if positioned earlier than the position of said persistent action indication.

17. The method of claim 12, wherein said primary tasks sequentially process messages transmitted thereto, and wherein said particular messages comprise at least the most recently processed message and all earlier messages transmitted by said primary tasks.

18. The method of claim 17, wherein said primary tasks sequentially process messages transmitted thereto, wherein said storing of transmitted messages is in a queue which stores transmitted messages in the order of transmission, wherein the performance of a persistent action indication at a position based no earlier than the position of the most recently processed message, and wherein said particular messages are chosen to be transmitted to said backup tasks prior to the performance of said persistent action based on the position of said persistent action indication in said queue.

19. The method of claims 12, wherein said particular messages are transmitted to said backup tasks such that each backup task receives each message of said particular messages which was transmitted to the respective primary task.

20. The method of claim 19, wherein said particular messages are transmitted to said backup tasks such that each backup task also receives each message of said particular messages which was transmitted by the respective primary task.

21. The method of claim 20, including each backup task providing a count of the number of messages received which were transmitted by the respective primary task.

22. The method of claim 21, wherein each backup processor uses said count during said recovering to determine when a message is to be transmitted.

23. The method of claim 22, wherein said checkpointing data includes a count of the number of messages processed by the primary task since the start or last checkpointing thereof, and wherein the respective backup task uses said count for discarding a corresponding number of messages.

* * * * *